US006568432B2

(12) United States Patent
Matsutani et al.

(10) Patent No.: US 6,568,432 B2
(45) Date of Patent: May 27, 2003

(54) METHOD FOR MANUFACTURING A STENT

(75) Inventors: Masaaki Matsutani, Tochigi-ken (JP);
Masatoshi Fukuda, Tochigi-ken (JP);
Shoichi Fukuda, Tochigi-ken (JP)

(73) Assignee: Mani, Inc., Tochigi-ken (JP)

( * ) Notice: Subject to any disclaimer, the term of this patent is extended or adjusted under 35 U.S.C. 154(b) by 0 days.

(21) Appl. No.: 09/916,299

(22) Filed: Jul. 30, 2001

(65) Prior Publication Data

US 2002/0033552 A1 Mar. 21, 2002

(51) Int. Cl.$^7$ ................................................ B21F 25/00
(52) U.S. Cl. ................................. 140/71 R; 623/1.19
(58) Field of Search ......................... 140/71 R, 92.1, 140/107; 623/1.15, 1.16, 1.2, 1.22, 1.32, 1.33, 1.18, 1.19

(56) References Cited

U.S. PATENT DOCUMENTS 5,554,181 A * 9/1996 Das ........................... 623/1.15
5,766,237 A * 6/1998 Cragg ........................ 623/1.15

* cited by examiner

Primary Examiner—Lowell A. Larson
(74) Attorney, Agent, or Firm—Townsend & Banta

(57) ABSTRACT

A stent manufactured for treating internal tubular organs, typically for treating a blood vessel, in which the stent has a sufficient diametral shrinkage ability and an ability for returning back to the original diameter thereof.

A zigzag shape-memorized stent A is manufactured by performing shape memorization where a wire 1 is fixed in a zigzag bent manner in which the wire is made from a shape-memorizing Ni—Ti alloy not having been subject to shape-memorization of any sort. A stent A being shape-memorized with a zigzag shape as well as a cylindrical shape could be manufactured by performing shape-memorization process in which a stent having been shape-memorized into a zigzag shape with the end portions thereof being connected by overlapping with each other, is attached to a cylindrical jig.

2 Claims, 4 Drawing Sheets

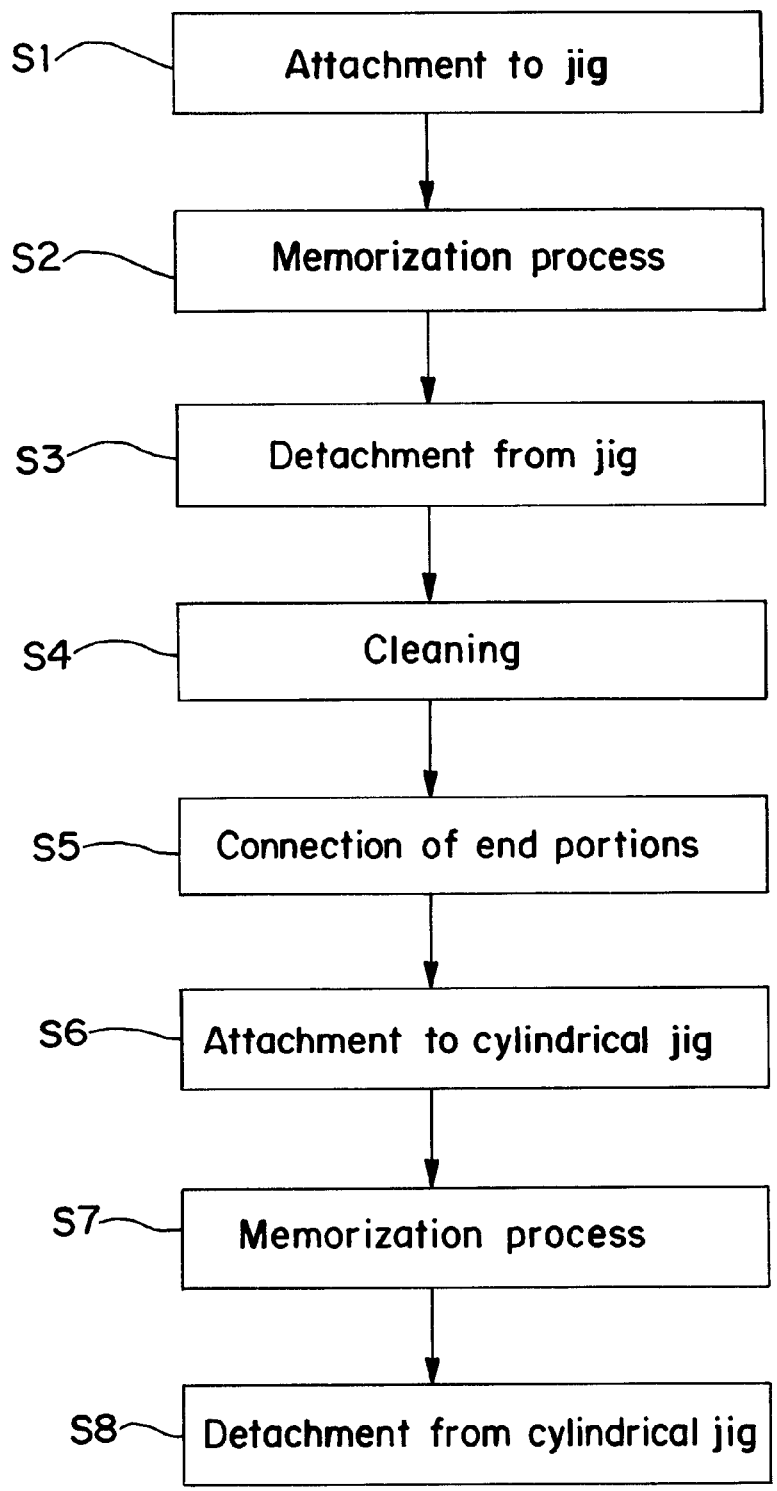
F I G. 1

METHOD FOR MANUFACTURING A STENT

BACKGROUND OF THE INVENTION

1. Field of the Invention

This invention relates to a method for manufacturing a stent for treating internal tubular organs such as a blood vessel and more particularly for treating aneurysm.

2. Description of Related Art

Inside a body, there are many tubular organs, such as a blood vessel, a bile duct, a ureter, an esophagus, or the like; such organs bear a possibility of characteristic ailments such as stenosis or occlusion. For example, in respect of blood vessels, there are possibilities of ailments such as stenosis, occlusion, aneurysm, varicosity, and the like. More particularly, since aneurysm is a serious ailment where a rupture of a blood vessel causes excessive bleeding, prompt treatment is to be required, and various tools have been developed for treating thus ailment effectively.

Lately, the use of a metallic cylindrical tool called a stent is increasingly used for treating a portion of blood vessel stenosis or for treating aneurysm. For example, when treating aneurysm, a stentgraf, which covers the stent with an artificial blood vessel, is used; such stentgraf is positioned in place at the inner side of the aneurysm so that pressure of blood would not affect the aneurysm.

As for examples regarding the kinds of stents, there is a cylindrical stent made from a metal material (representatively from stainless steel) or a stent having a metal wire bent in a zigzag manner while at the same time having a cylindrical shape. Such stents are delivered to an affected portion internally through a blood vessel and positioned in place when reaching the affected portion.

In a case of positioning the stent at the affected portion, the stent is diametrally shrunk and confined within a long tubular delivery kit, in which the delivery kit has a guiding wire inserted therethrough; and then, starting from the guiding wire, the delivery kit is guided through a blood vessel from a portion such as the root of a leg till reaching the affected portion, and then, when reaching the affected portion, the delivery kit is retracted to release the stent from confinement. After being released from confinement, the stent diametrally self-expands, and is positioned in place at the affected portion in thus expanded state for protecting the blood vessel.

When the stent is released from confinement as mentioned above, it would be necessary for the stent to precisely return back to the original diameter (diameter before diametral shrinkage). If the return back to the original diameter lacks precision, preparation of a stent with a diameter anticipating the rate of returning back would become necessary and would cause the requirement of extra labor and material.

Meanwhile, as for zigzag shaped stents, various shapes thereof have been proposed as shown in FIG. 5. A stent 51 shown in FIG. 5(a) is structured having numerous short members 51 a welded at the end portions thereof. Although the stent 51 has a characteristic of being easily diametrally shrunk, the material for the member 51a will be limited owing to the requirement of a welding procedure. A stent 52 shown in FIG. 5(b) is structured with a single wire having a relatively large bending radius. Although the stent 52 has a characteristic of being resistant to fracture owing to a low degree of processing, the stent 52 has a difficulty of being diametrally shrunk, A stent 53 shown in FIG. 5(c) is structured with a single wire having a relatively small bending radius. Although the stent 53 has a characteristic of being easily diametrally shrunk, the stent has a problem of being easily fractured owing to a high degree of processing.

Although stainless steel is typically used as a material for the stent as mentioned above, a stainless steel stent raises a problem of not being able to sufficiently return back to the original diameter after being released from confinement, in a case when the elasticity limit for stainless steel is exceeded during diametral shrinkage.

Accordingly, it is preferable for a shape-memorizing alloy of Nickel (Ni) and Titanium (Ti) to be used as the material for the stent instead of stainless steel, since the alloy is: durable against repetitive force when in a range exceeding elasticity; corrosion-resistant; and safe upon the living body.

However, when attempting to manufacture the foregoing zigzag shaped stents 51 through 53 with use of a shape-memorizing alloy comprised of Nickel and Titanium, the stent 51 could not be applied upon, owing to the requirement of welding. Further, in respect of the stent 52, owing to the large bending radius, a wire diameter could be thickened to allow high rigidity; nevertheless, containment into the delivery kit would be difficult since diametral shrinkage is difficult to be performed. Further, in respect of the stent 53, owing to the high diametral shrinkage ability of the stent 53, containment into the delivery kit could be performed easily, nevertheless, reduction of a bending radius during a bend-processing would heighten the degree of processing to raise the possibility of causing fracture.

Due to the foregoing problems, conventionally, it was difficult to manufacture a zigzag shaped stent using a wire made from a shape memorizing alloy of Nickel and Titanium which could satisfy the conditions of being able to diametrally shrink with ease and being difficult to become fractured.

It is an objet of this invention to provide a method of manufacturing a stent using a shape-memorizing alloy comprised of Nickel and Titanium, in which the stent is capable of reducing a bending radius and is therefore capable or enabling sufficient diametral shrinkage.

SUMMARY OF THE INVENTION

The present inventor has attempted various experiments for developing a method of manufacturing a stent by bend-processing a wire made from a shape-memorizing alloy of Nickel and Titanium. As a result, it has been found that the possibility of fracture during a process of bending the wire made from the Ni—Ti alloy depends on the difference in the past history of the wire.

An experiment have been performed where wires of equal thickness are bent into a same radius, in which one wire is made of a material being shape-memorized with a straight line shape, and the other wire is made of a material not having been shape-memorized. The experiment has tested whether or not fracture will occur during a process of detaching the wires from a jig and returning the wires back to the straight line shape after the wires have been shape-memorized into respective bending radiuses, under the conditions that: the datum for each item is 5; the bending radius ranges from 0.1 mm through 0.6 mm; and the thickness of the wire are respectively 0.3 mm, 0.4 mm, 0.5 mm. The result for the experiment is shown in chart 1. In chart 1, an X mark is applied when there is one or more fractured wires within datum 5, and a circle mark is applied when all of five are not fractured.

CHART 1

(*) fractured during forming R = 0.1
X: 1 or more wires of 5 wires fractured   ○: all 5 wires not fractured
N = 5

| φd−φ0.3 mm | | | φd−φ0.4 mm | | | φd−φ0.5 mm | | |
|---|---|---|---|---|---|---|---|---|
| | whether or not fracture would occur after being heated, detached from jig, and spread 180° | | | whether or not fracture would occur after being heated, detached from jig, and spread 180° | | | whether or not fracture would occur after being heated, detached from jig, and spread 180° | |
| R (mm) | with straight line memory | without straight line memory | R (mm) | with straight line memory | without straight line memory | R (mm) | with straight line memory | without straight line memory |
| 0.1 | X (*) | ○ | 0.1 | X | X | 0.1 | X | X |
| 0.2 | ○ | ○ | 0.2 | X | ○ | 0.2 | X | X |
| 0.3 | ○ | ○ | 0.3 | ○ | ○ | 0.3 | X | ○ |
| 0.4 | ○ | ○ | 0.4 | ○ | ○ | 0.4 | X | ○ |
| 0.5 | ○ | ○ | 0.5 | ○ | ○ | 0.5 | ○ | ○ |
| 0.6 | ○ | ○ | 0.6 | ○ | ○ | 0.6 | ○ | ○ |

As the results shown in chart 1, the wire already having been shape-memorized is more likely to fracture at a level of a larger radius compared to the wire not having been subject to shape-memorization.

Accordingly, the method of manufacturing a stent regarding this invention is a method of manufacturing a zigzag shaped stent made from a shape-memorizing alloy comprised of nickel and titanium, wherein the method serves to perform shape-memorization of a zigzag shape by using a shape-memorizing alloy made wire not having been subject to shape-memorization.

With this method of manufacturing a stent, a process of bending into a small radius could be achieved for enabling memorization of the bent shape by using a wire made from a shape-memorizing alloy of Nickel and Titanium (Ni—Ti). Accordingly, a zigzag shaped stent with a small bending radius could be reasonably manufactured without fracture.

Another method of manufacturing a stent regarding this invention is a method of manufacturing a zigzag shaped stent made from a shape-memorizing alloy comprised of nickel and titanium, comprising the steps of: performing a zigzag shape-memorization process in which a shape-memorizing alloy wire not having been subject to shape-memorization is fixed upon a jig in a zigzagging manner; and performing a cylindrical shape-memorization process in which the shape-memorizing alloy wire having been subject to the zigzag shape-memorization is fixed to a cylindrical jig in a wrapping manner.

With this method of manufacturing a stent, a process of bending into a small radius could be achieved for enabling memorization of the bent shape by using a wire made from a shape-memorizing alloy of Nickel and Titanium (Ni—Ti); and also enable the wire having memorized the bent shape to further memorize a cylindrical shape. Accordingly, a cylindrical shaped stent with a small bending radius could be reasonably manufactured.

BRIEF DESCRIPTION OF THE DRAWINGS

The above and other objects and features of the invention are apparent to those skilled in the art from the following preferred embodiments thereof when considered in conjunction with the accompanied drawings, in which:

FIG. 1 is a flow chart for explaining a manufacturing process;

DESCRIPTION OF THE PREFERRED EMBODIMENTS

Figure 2:
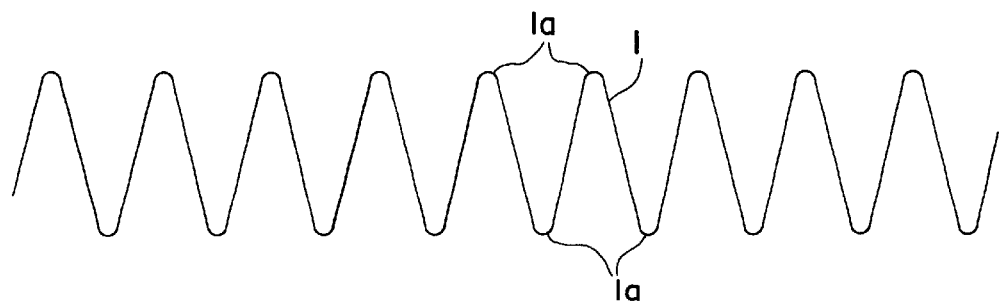
FIG. 2 is a drawing for explaining a shape of a zigzag shaped stent.
Figure 3:
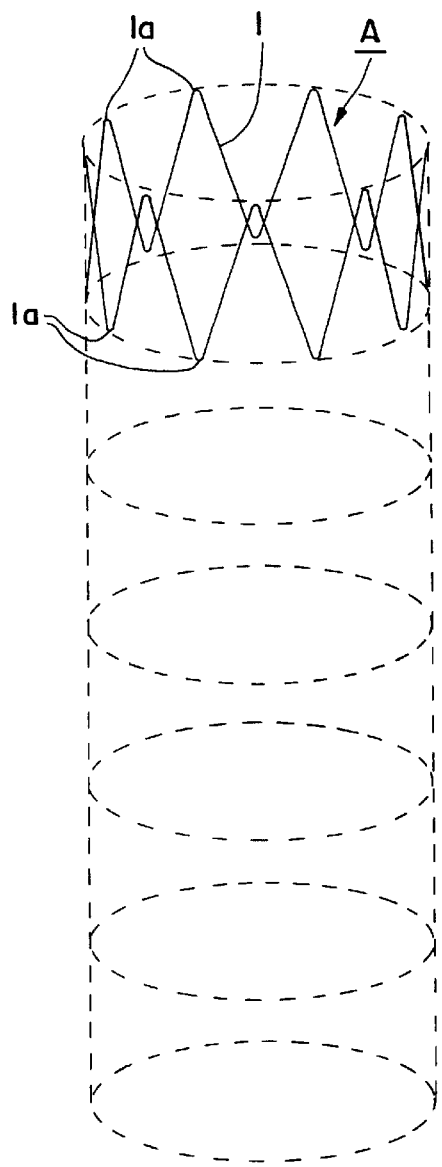
FIG. 3 is a drawing for explaining a shape of a cylindrical stent.
Figure 4:
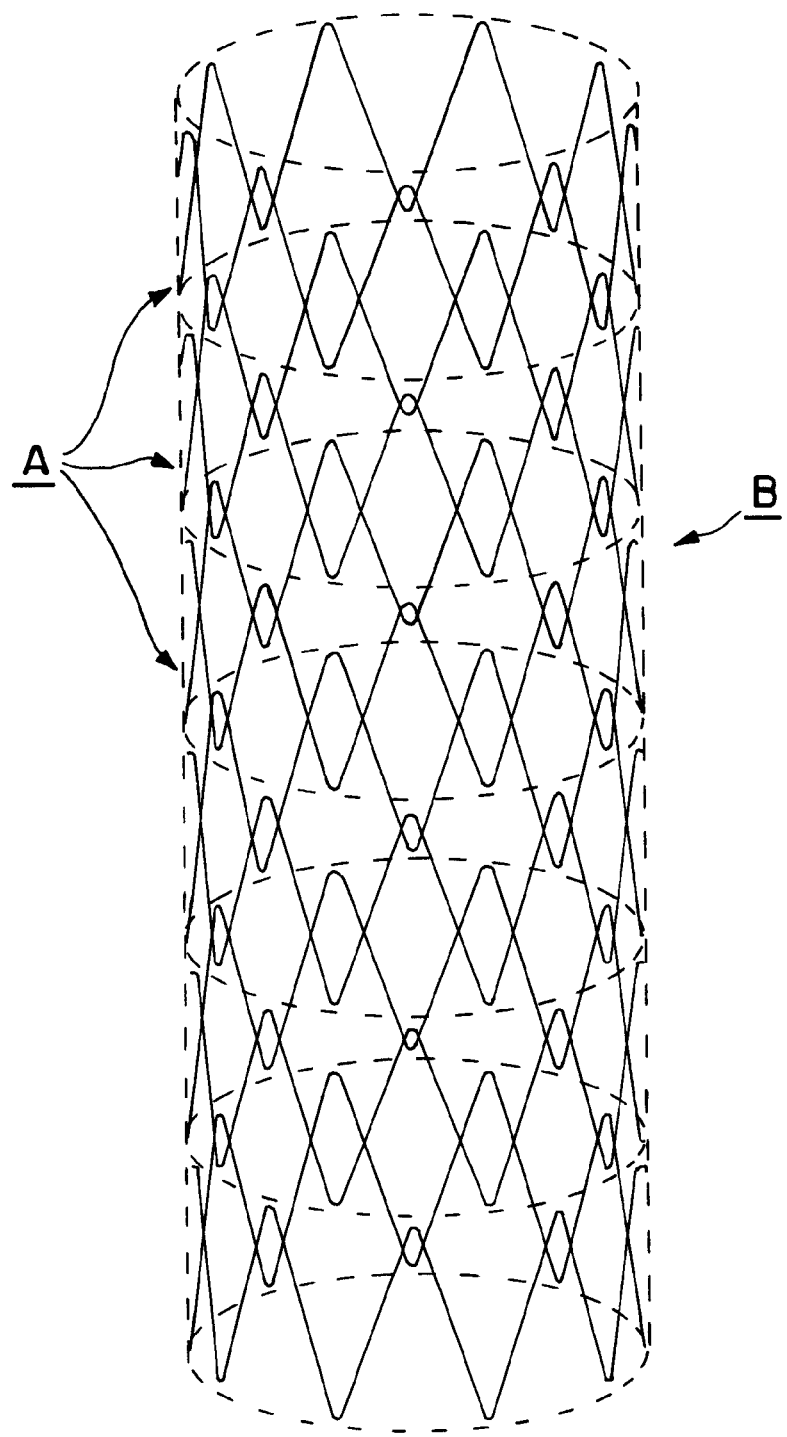
FIG. 4 is a drawing for explaining plural stents continuing in a longitudinal direction.
Figure 5A:
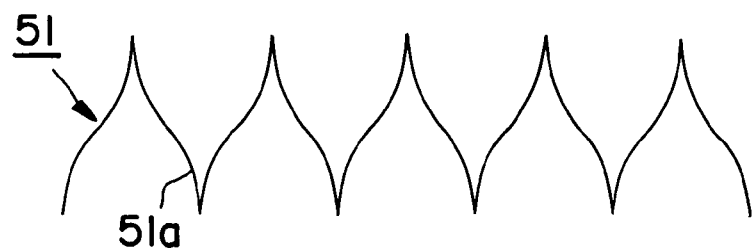
FIG. 5 is a drawing for explaining an example of a zigzag shaped stent.
Figure 5B:
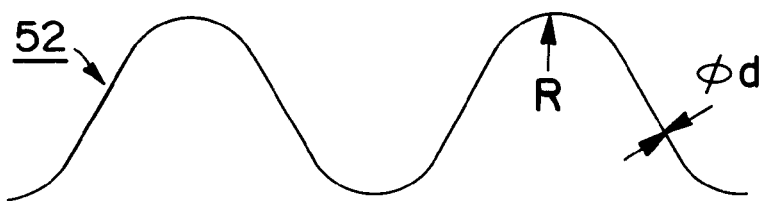
Figure 5C:
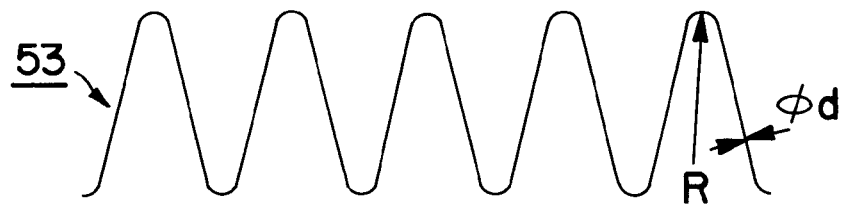

A preferable embodiment of this invention regarding a method for making a stent will hereinafter be described with reference to the drawings. FIG. 1 is a flow chart showing a manufacturing process. FIG. 2 is a drawing for explaining a shape of a zigzag-like stent. FIG. 3 is a drawing for explaining a shape of a cylindrical stent. FIG. 4 is a drawing for explaining plural stents continuing in a longitudinal direction.

Regarding this embodiment of a stent manufacturing method, a memorization process is performed in which, a wire made from a shape-memorizing alloy of nickel (Ni) and titanium (Ti) is processed into a zigzag shape by means of bending, and then the wire is heated in a prescribed manner while maintaining the zigzag shape of the wire; such wire made from the shape-memorizing alloy is limited to a wire not yet subject to shape-memorization so as to allow a steady manufacturing of the stent in which fracture of the wire could be prevented even when the bending radius is small during the process of bending.

Before describing the stent manufacturing method, the shape of the stent will be described with reference to FIG. 4. In the drawing, a stent A is structured in a manner where a wire 1 made from a shape-memorizing alloy of nickel and titanium is shape-memorized by being bent into a zigzag shape, and allowing the zigzag shape-memorized wire 1 to be further shape-memorized with a cylindrical shape.

The stent A is formed with a diameter corresponding to an organ or portion subject for treatment, and the stent A is formed with a substantially fixed length. Accordingly, in a case where the portion subject for treatment is of a long length, a combined body B comprising a plurality of stents A are formed by arranging and connecting such plural stents A with each other in a longitudinal direction (axial direction); such combined body B is placed at the affected portion for enabling treatment.

Especially when treating aneurysm, a stentgraft is formed by covering an artificial blood vessel upon the combined body B; such stentgraft is placed at a portion subject for treatment so as to achieve treatment by removing the stress upon the aneurysm.

The stent A of this embodiment functions to treat aneurysm, and is set with a diameter of 50 mm, and a length of approximately 25 mm.

There are no particular restrictions regarding the thickness of the wire 1 for the stent A the thickness of the wire is chosen depending on the ability of withstanding the force applied upon an affected portion subject for positioning the stent A. In this embodiment, the wire 1 for the stent A is comprised of nickel (Ni) and titanium (Ti) in which nickel is of 56.06% weight and the remaining thereof is titanium; the wire has a black leather surface with a diameter of 0.4 mm, and further, the wire is in a state not yet subject to any kind of shape-memorization.

Next, the process of manufacturing the stent A will be explained hereinafter with reference to FIG. 1 through FIG. 3. First, the past history of the wire 1 is examined so as to confirm that the wire I has not yet been subject to any kind of shape-memorization; this procedure is performed by means such as by obtaining a guarantee by a material maker. It is unfavorable to remove the memory of the wire 1 since the strength of the material would deteriorate.

Accordingly, the wire 1 guaranteed of not yet being subject to any kind of shape-memorization is cut into a length required for manufacturing the stent A. For example, when manufacturing under the circumstance where a cylindrical stent A has a 50 mm diameter, a 25 mm length, 9 zigzagging mountain peaks, the wire 1 would be required to be cut into a length of approximately 500 mm for making the stent A.

In step S1, the cut wire 1 is attached to a plane surface jig (not shown) and is formed in zigzagging manner as shown in FIG. 2. In such case, it is preferable to make the length of the zigzagging portion equal to or slightly shorter than the length of a spread out stent, in order to prevent an excessive oversupply when forming the cylindrical shape.

The zigzagging mountain portion (mountain portion 1a) is bent by hooking upon a fixed pin having a predetermined bending radius, so that each mountain portion 1a could be processed with having a substantially equal radius. The smaller the bending radius of the mountain portion 1a is, the higher the diametral shrinkage of the wire would become and the easier the fracture of the wire would become; the larger the bending radius of the mountain portion 1a is, the poorer the diametral shrinkage of the wire would become and the more difficult the fracture of the wire would become. Therefore, the bending radius of the mountain portion 1a is set in accordance to circumstance with respect to the conditions of the organs and the portions subject for treatment. In this embodiment, the bending radius of the mountain portion 1a is set to 0.5 mm. Accordingly, the diameter of the pin is 1 mm.

After the wire 1 is in a state attached and fixed to the jig in step S1, a memorization process is then performed in step S2, while maintaining thus state. The memorization process for the shape-memorizing alloy of Ni—Ti is a heating process in which, the wire is maintained for a prescribed time within a vacuum-heating furnace set with a temperature ranging from 400° C. through 550° C., and then, the wire is cooled.

In this embodiment the memorization process is performed by combining the following conditions in which, a vacuum degree of the vacuum-heating furnace is set to approximately $10^{-2}$ through $10^{-3}$ Pa, the temperature is set to 400° C., 450° C., 500° C., 550° C., and the processing time is performed in 30 minutes, 60 minutes.

By performing the memorization process under the foregoing conditions, returning back to the memorized shape within the body could be sufficiently accomplished. Accordingly, the wire 1 having memorized the zigzag shape upon a flat surface is cut in accordance to circumstance, wherein each of the end portions of the wire 1 are connected to complete a cylindrical functioning stent A.

Although the foregoing jig is structured for allowing a zigzag shape upon a flat surface, the jig could be formed into a cylindrical shape and allow a zigzag shape upon such cylindrical shape. However, also in this case, the shape-memorization process for the cylindrical stent A should preferably be performed in a latter process; this is due to the fact that the connecting among the end portions of the wire 1 should preferably be performed after the zigzag shape-memorization process in a state detached from the jig.

Since the wire 1 is not yet subject to any kind of shape-memorization, the wire 1 will not break apart even if the mountain portion 1a is formed with a small radius, a zigzag stent A having a high shrinking ability could be manufactured.

After being fixed upon the jig and being subject to shape-memorization in step S2, the wire 1 is detached from the jig in step S3.

After being detached from the jig in step S3, the wire 1 is cleaned in step S4. Step S4 is a process aimed to remove the black skin on the surface of the wire 1; in which the process of removing black skin by acid cleansing or by electrolytic polishing, neutralization, water cleansing, and drying are included in step S4 Nevertheless, the process of cleaning the wire 1 is not mandatory, and further, the cleaning could be performed in a latter process.

Following step S4, the wire 1 having been memorized with a zigzag shape is then subject to a process of memorizing a cylindrical shape. In step S5, two unengaged end portions of the zigzag wire 1 are overlapped and connected to each other. As for methods for performing the connection, there are a spot welding method, and a pure titanium wire binding method, in which the methods could be used individually or in a combined manner.

For example, in a case using the spot welding method, connection could be achieved sufficiently by welding two through five overlapped portions of the wire 1. Since the welding portions take up a small share compared to that of the entire length of the stent A, the welding would not have much effect on the stent A, and would not any bad influence in terms of functioning as a stent. In a case using the pure titanium wire binding method, connection could be achieved sufficiently by a pure titanium wire of approximately 0.2 mm, or two or five rolls of a 0.4 mm×0.2 mm flat wire being bound in two or four portions.

By connecting the end portions of the wire 1 with each other, the wire 1 is formed into a stent A having a cylindrical shape. Nevertheless, even if the zigzag wire 1 is rolled up, the wire 1 could not be a circle of a high precision, and further, the diameter of the wire 1 would often be different from the prescribed diameter of the stent A.

In step S6, the wire 1 is attached to a cylindrical jig (not shown in drawing). The cylindrical jig has an outer diameter to form a prescribed diameter for the stent A; after the stent A with connected end portions is wrapped around the jig, the jig is suitably tightened with a flexible, heat resistant member such as a metal wire, a metal band or the like. Accordingly, as shown in FIG. 3, the stent 3 could be restrained to have a cylindrical shape with a prescribed diameter.

Further, before advancing to a memorization process of step S7 in which the stent A is transferred to the heating furnace, the stent A attached to the cylindrical jig would not slip and would enable maintaining the attached shape.

In step S7, the stent A being attached to the cylindrical jig is subject to shape-memorization in which the stent A is memorized into a cylindrical shape. This shape-memorization is performed under the same conditions as in step S2. In other words, the stent A being attached to the cylindrical jig is shape-memorized by being placed inside a vacuum heating furnace, then heated in a temperature ranging from 400° C. through 550° C. for a prescribed period, and then cooled.

By performing the shape-memorization, the stent A is memorized with a zigzag shape and a cylindrical shape, and would be capable of returning back to the memorized shape in FIG. 3 when heated above the temperature of a shape-returning point (Af point). Accordingly, for example, when the stent A is restrained in a state where a diameter of the stent A is retracted by being folded or by having a periphery of the stent A bent toward a center, the stent A could return back to a combined form of a zigzag shape and a cylindrical shape, when such restraint is released and the temperature is raised no less than the Af point.

Other than using the vacuum-heating furnace for memorization as in step S2 and step S7, a salt bath or argon gas atmosphere could be used as the heating furnace.

Following the memorization process of step .S7, the stent A is detached from the cylindrical jig in step S8 so as to manufacture the stent A shown in FIG. 3.

Even having memorized the combined shape of a zigzag shape and a cylindrical shape, the stent A being manufactured through the foregoing process could be formed having a zigzagging mountain portion 1a with a small bending radius, owing to the fact that the zigzag shape-memorization is applied upon the wire 1 not yet being subject to shape-memorization. Accordingly, the manufactured stent A could achieve an excellent diametral shrinkage ability, and could perform the characteristic of the shape-memorizing alloy such as being highly capable of returning to the original diameter.

The diameter and the length for the foregoing manufactured stent A are predetermined. During the use of the stent A, in correspondence with the length of an affected portion, plural stents A are connected in an axial direction for forming the combined body B shown in FIG. 4; then, the combined body B is contained in a restrained state inside a delivery kit and transported to the affected portion; then after reaching to the affected portion, the combined body B is taken out from the delivery kit and released from the constrained state for returning back to the memorized shape in means to be placed inside the aneurysm; subsequently, the pressure applied upon the affected portion could be withstood.

As described above, in respect of the stent manufacturing method for this invention, a zigzag shaped stent could be manufactured by shape-memorizing a zigzag form upon a wire made from a shape-memorizing alloy of Nickel and Titanium. More particularly, the bending radius for the zigzagging mountain portion could be reduced by using a wire made from a shape memorizing alloy, which is not yet subject to shape-memorization; accordingly the bending radius regarding the mountain portion of the stent could be reduced as much as possible, and the stent could have a sufficient diametral ability.

As for another manufacturing method regarding this invention, a wire made from a shape memorization alloy, which has not yet been subject to any sort of shape-memorization, is shape-memorized into a zigzag shape, and is then shape-memorized into a cylindrical shape in means to allow the memorization of the zigzag shape with a small bending radius, which had been memorized in the initial memorization process. Therefore, a cylindrical stent with high diametral shrinkage ability comprised of a mountain portion with a small bending radius could be manufactured.

In other words, even having been memorized with a zigzag shape and a cylindrical shape, the zigzag mountain portion of the stent could be formed with an extremely small bending radius. Further, the wire of the stent would seldom fracture during manufacture, and the stent could be manufactured having a high yield rate with a uniform quality.

The foregoing description of a preferred embodiment of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined by the claims set forth below.

What is claimed is:

1. A method of manufacturing a zigzag shaped stent made from a shape-memorizing alloy comprised of nickel and titanium, wherein the method performs shape-memorization of a zigzag shape by using a shape-memorizing alloyed wire not having been subject to shape-memorization with a straight shape.

2. A method of manufacturing a zigzag shaped stent made from a shape-memorizing alloy comprised of nickel and titanium, comprising the steps of:
   performing a zigzag shape-memorization process in which a shape-memorizing alloyed wire not having been subject to shape memorization is fixed upon a jig in a zigzag manner;
   detaching the zigzag wire from the jig and overlapping and connecting two unengaged end portions of the zigzag wire, and
   performing a cylindrical shape-memorization process in which the shape-memorizing alloyed wire having been subject to the zigzag shape-memorization is fixed to a cylindrical jig in a wrapping manner.

* * * * *

UNITED STATES PATENT AND TRADEMARK OFFICE
CERTIFICATE OF CORRECTION

PATENT NO. : 6,568,432 B2
DATED : May 27, 2003
INVENTOR(S) : Matsutani et al.

It is certified that error appears in the above-identified patent and that said Letters Patent is hereby corrected as shown below:

<u>Title page,</u>
Please insert Item -- [30], Foreign Priority Document No.
        Jul. 31, 2000   (JP)................................2000-231265 --

Signed and Sealed this

Fourth Day of November, 2003

JAMES E. ROGAN
*Director of the United States Patent and Trademark Office*